(12) United States Patent
Petit

(10) Patent No.: US 10,967,140 B2
(45) Date of Patent: Apr. 6, 2021

(54) DEVICE FOR DISPENSING A FLUID PRODUCT SYNCHRONISED WITH INHALATION

(71) Applicant: APTAR FRANCE SAS, Le Neubourg (FR)

(72) Inventor: Ludovic Petit, Vitot (FR)

(73) Assignee: APTAR FRANCE SAS, Le Neubourg (FR)

( * ) Notice: Subject to any disclaimer, the term of this patent is extended or adjusted under 35 U.S.C. 154(b) by 171 days.

(21) Appl. No.: 16/093,305

(22) PCT Filed: Apr. 13, 2017

(86) PCT No.: PCT/FR2017/050895
§ 371 (c)(1),
(2) Date: Oct. 12, 2018

(87) PCT Pub. No.: WO2017/178768
PCT Pub. Date: Oct. 19, 2017

(65) Prior Publication Data
US 2019/0175850 A1 Jun. 13, 2019

(30) Foreign Application Priority Data
Apr. 15, 2016 (FR) ...................................... 1653367

(51) Int. Cl.
*A61M 15/00* (2006.01)
*A61M 16/00* (2006.01)

(52) U.S. Cl.
CPC ...... *A61M 15/0095* (2014.02); *A61M 15/008* (2014.02); *A61M 15/009* (2013.01);
(Continued)

(58) Field of Classification Search
CPC .............. A61M 15/00; A61M 15/0001; A61M 15/0013; A61M 15/0021; A61M 15/08;
(Continued)

(56) References Cited

U.S. PATENT DOCUMENTS 3,732,864 A * 5/1973 Thompson .......... A61M 15/009
128/200.23
4,664,107 A * 5/1987 Wass .................. A61M 15/0091
128/200.23

(Continued)

FOREIGN PATENT DOCUMENTS

DE 30 40 641 A1 5/1982
EP 0 441 643 A1 8/1991
(Continued)

OTHER PUBLICATIONS

International Preliminary Examination Report of PCT/FR2017/050895 dated Oct. 18, 2018.
(Continued)

Primary Examiner — Joseph D. Boecker
(74) Attorney, Agent, or Firm — Sughrue Mion, PLLC

(57) ABSTRACT

An inhalation-synchronized fluid dispenser device having a body provided with a mouthpiece, a fluid reservoir containing a fluid and a propellant gas mounted to slide axially, a metering valve including a valve member assembled on the reservoir for selectively dispensing the fluid. The device also includes an actuator element movable and/or deformable between a non-actuation position and an actuation position; and an inhalation-controlled trigger system including an inhalation-sensitive member deformable and/or movable under the effect of inhaling so as to move and/or deform the actuator element from its non-actuation position towards its actuation position. The actuator element is a locking element that, in its non-actuation position, enables the valve member of the metering valve to move axially in the body together
(Continued)

with the reservoir, preventing said metering valve from being actuated when the reservoir is moved axially in the body without inhaling.

13 Claims, 1 Drawing Sheet

(52) U.S. Cl.
CPC ..... *A61M 15/0021* (2014.02); *A61M 15/0025* (2014.02); *A61M 2016/0021* (2013.01); *A61M 2205/276* (2013.01); *A61M 2205/3331* (2013.01); *A61M 2205/3553* (2013.01); *A61M 2205/3561* (2013.01); *A61M 2205/3584* (2013.01); *A61M 2205/3592* (2013.01); *A61M 2205/502* (2013.01); *A61M 2205/52* (2013.01)

(58) Field of Classification Search
CPC ............ A61M 15/009; A61M 15/0091; A61M 15/0095; A61M 15/0096; A61M 11/00; A61M 11/04; A61M 11/08
See application file for complete search history.

(56) References Cited

U.S. PATENT DOCUMENTS

| | | | | |
|---|---|---|---|---|
| 5,060,643 | A | | 10/1991 | Rich et al. |
| 5,069,204 | A | * | 12/1991 | Smith ............... A61M 15/0068 128/200.23 |
| 5,347,998 | A | * | 9/1994 | Hodson ............ A61M 15/0091 128/200.23 |
| 2017/0065777 | A1 | * | 3/2017 | Koerner ................ H01L 41/083 |
| 2019/0130790 | A1 | * | 5/2019 | Baker .................... G09B 19/24 |

FOREIGN PATENT DOCUMENTS

| | | |
|---|---|---|
| FR | 2 775 668 A1 | 9/1999 |
| WO | 85/01880 A1 | 5/1985 |

OTHER PUBLICATIONS

International Search Report PCT/FR2017/050895 filed Jul. 31, 2017.

* cited by examiner

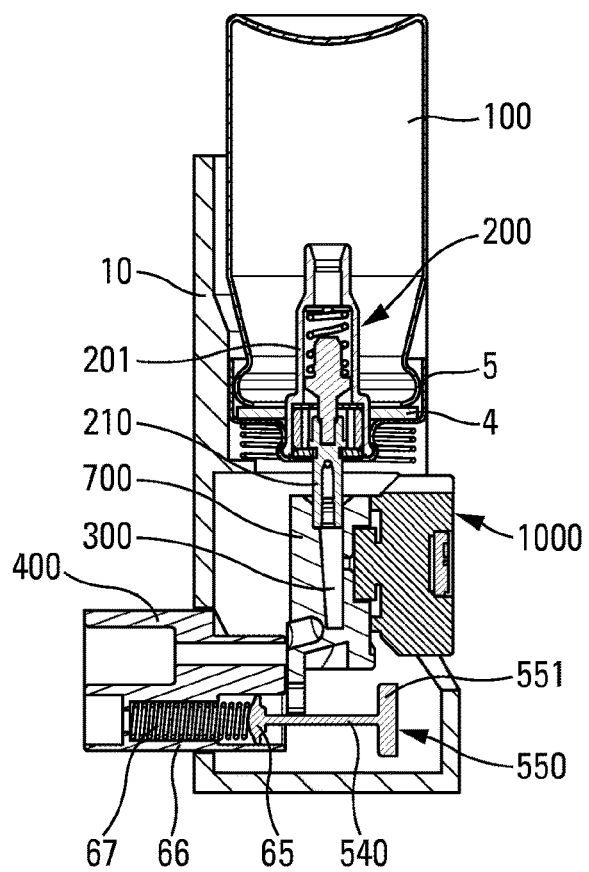
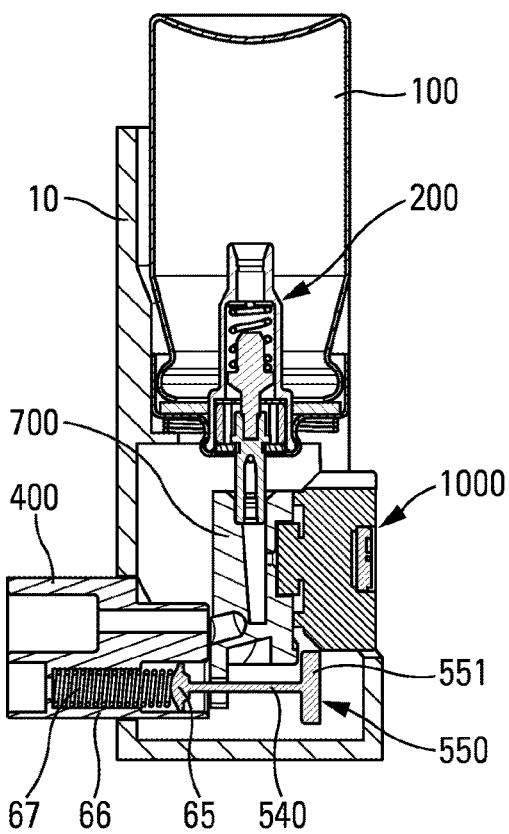
Fig. 1
Fig. 2
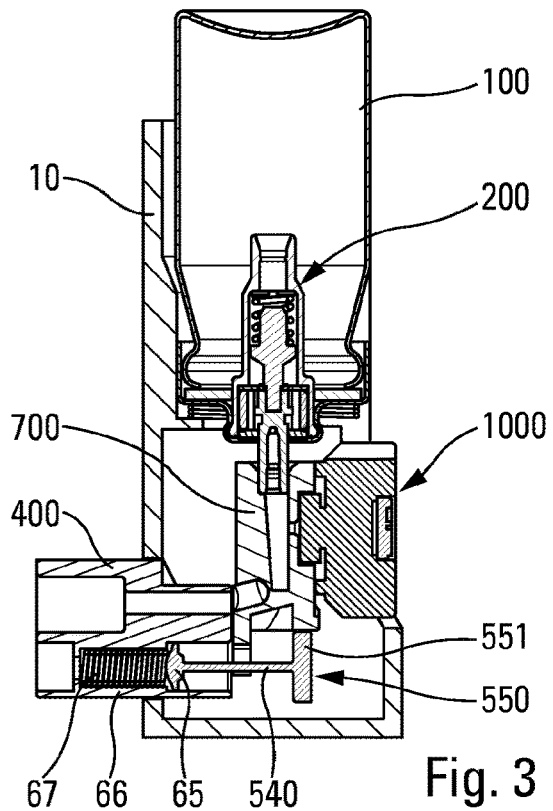
Fig. 3

DEVICE FOR DISPENSING A FLUID PRODUCT SYNCHRONISED WITH INHALATION

This application is a National Stage of International Application No. PCT/FR2017/050895 filed Apr. 13, 2017, claiming priority based on French Patent Application No. 1653367 filed Apr. 15, 2016.

The present invention relates to a fluid dispenser device in which dispensing is synchronized with inhaling, and more particularly it relates to an inhaler device of the aerosol type synchronized with inhaling.

Breath actuated inhaler (BAI) devices are well known in the state of the art. The main advantage of this type of device is that the dispensing of fluid is synchronized with the patient inhaling, so as to guarantee that the fluid is properly dispensed into the airways. Thus, in the field of aerosol devices, i.e. devices in which the fluid is dispensed by means of a propellant gas, numerous types of breath actuated inhaler device have been proposed. However, those devices present the drawback of including a large number of parts, i.e. they are complicated and costly to manufacture and to assemble, which is obviously disadvantageous. It is also difficult to find the right balance between reliable triggering on each inhalation, without the actuation threshold being too high, and a latch that is robust enough to prevent accidental of unwanted actuation. Unfortunately, when the latch releases accidentally, the device is actuated automatically and the dose is dispensed, even when the user does not want it.

Thus, in order to dispense the dose properly, what is more important than actuating the device automatically, is for dispensing to be synchronized with the user inhaling, even if actuation or triggering remains manual.

Document FR 2 775 668 describes a prior-art device.

An object of the present invention is to provide an inhalation-synchronized fluid dispenser device that does not have the above-mentioned drawbacks.

Another object of the present invention is to provide an inhalation-synchronized fluid dispenser device that improves operational reliability by guaranteeing effective actuation on each inhalation.

Another object of the present invention is to provide an inhalation-synchronized fluid dispenser device that minimizes the risks of accidental or unwanted actuation.

Another object of the present invention is to provide an inhalation-synchronized fluid dispenser device that does not present an actuation threshold that is too high, thereby making it possible for people who are relatively weak, such as the sick or the elderly, to use the device in safe and reliable manner.

Another object of the present invention is to provide an inhalation-synchronized fluid dispenser device that is simple and inexpensive to manufacture and to assemble.

The present thus provides an inhalation-synchronized fluid dispenser device comprising a body provided with a mouthpiece, a fluid reservoir containing a fluid and a propellant gas being mounted to slide axially in said body, a metering valve including a valve member being assembled on said reservoir for selectively dispensing the fluid, said device further comprising:
an actuator element that is movable and/or deformable between a non-actuation position in which said metering valve cannot be actuated, and an actuation position in which said metering valve can be actuated; and
an inhalation-controlled trigger system including an inhalation-sensitive member that is deformable and/or movable under the effect of inhaling, said inhalation-sensitive member, when it is deformed and/or moved, moving and/or deforming said actuator element from its non-actuation position towards its actuation position, said actuator element being a locking element that, in its non-actuation position, enables said valve member of the metering valve to move axially in the body, together with said reservoir, preventing said metering valve from being actuated when said reservoir is moved axially in the body without inhaling.

Advantageously, during inhaling, said locking element is moved and/or deformed so that it prevents the valve member from moving axially relative to the body.

Advantageously, said inhalation-controlled trigger system includes a piston that slides in a chamber between a rest position and an inhaling position.

Advantageously, said locking element is secured to a rod that is secured to the piston, so that during inhaling, said rod moves radially, moving said locking element towards its actuation position in which it prevents said valve member of the metering valve from moving axially when said reservoir is moved axially in the body.

Advantageously, said device includes an electronic dose counter.

Advantageously, said device includes signal-transmitter means for communicating, in particular communicating remotely, information relating to the actuations of the device.

These characteristics and advantages and others appear more clearly from the following detailed description, given by way of non-limiting example, and with reference to the accompanying drawing, in which:

FIG. 1 is a diagrammatic section view of a fluid dispenser device, in an advantageous embodiment, in the rest position;

FIG. 2 is a view similar to the view in FIG. 1, when the user attempts to actuate the device without inhaling; and FIG. 3 is a view similar to the view in FIG. 2, when the user actuates the device while inhaling simultaneously.

In the description, the terms "top", "bottom", "upwards", and "downwards" refer to the upright position of the device shown in particular in FIG. 1. The terms "axial" and "radial" are relative to the vertical central axis. The terms "proximal" and "distal" are relative to the mouthpiece.

The invention applies more particularly to inhaler devices of the aerosol-valve type for oral dispensing, as described in greater detail below, but it could also apply to other types of inhaler device, e.g. of the nasal type.

The figures show an advantageous embodiment of the invention, but naturally one or more of the component parts described below could be made in some other way, while providing functions that are similar or identical.

With reference to the drawing, the device includes a main body 10 provided with a mouthpiece 400. The mouthpiece 400 defines a dispenser orifice through which the user inhales while the device is being used. A removable protective cap may be provided on said mouthpiece 400, in particular while it is being stored, that the user removes before use. The body 10 contains a reservoir 100 that contains the fluid to be dispensed and a propellant gas, such as a gas of the hydrofluoroalkane (HFA) type, a metering valve 200 being mounted on said reservoir 100 for selectively dispensing the fluid. The metering valve 200 comprises a valve body 201, and a valve member 210 that, during actuation, is axially movable relative to said valve body 201, and thus relative to said reservoir 100. The metering valve 200 can be of any appropriate type. It may be fastened to the reservoir 100 via a fastener element, preferably a crimped cap 5, preferably with a neck gasket 4 interposed therebetween.

Advantageously, during actuation, the valve member 210 is stationary relative to the body 10, and it is the reservoir 100 that is moved axially relative to the body 10 between a distal position, which is the rest position, and a proximal position.

The outlet orifice of the valve member 210 of said metering valve 200 is connected via a channel 300 to said mouthpiece 400 through which the user inhales the fluid to be dispensed. In known manner, said valve member 210 is received in a valve well 700 that defines said channel 300, at least in part. Said valve well is axially movable relative to said body 10.

In the invention, the device includes an actuator element 550 that is movable and/or deformable between a non-actuation position in which said metering valve 200 cannot be actuated, and an actuation position in which said metering valve 200 can be actuated. In the rest position, said actuator element 550 is in the non-actuation position, and it is the user inhaling through the mouthpiece 400 that moves and/or deforms said actuator element 550 towards its actuation position. In other words, so long as the user does not inhale, it is impossible to actuate the metering valve 200, and it is only when the user inhales that said metering valve 200 can be actuated, advantageously by pressing manually on the bottom of the reservoir 100.

In the invention, the actuator element is a locking element 550 that, in its non-actuation position, enables the valve member 210 of the metering valve 200 to move axially in the body 10, together with said reservoir 100, thereby preventing said metering valve 200 from being actuated when said reservoir 100 is moved axially in the body 10 without inhaling. During inhaling, the locking element 550 is moved and/or deformed so that it prevents the valve member 210 from moving axially relative to the body 10. Thus, after inhaling, axial movement of the reservoir 100 causes the metering valve 200 to be actuated and a dose of fluid to be dispensed, synchronously with the inhaling.

Thus, in the absence of inhaling, there is no risk of an active dose of fluid being lost by accidental or incomplete actuation during which the user does not inhale. Actuating the valve 200 and expelling a dose of fluid are thus possible only when the user inhales and simultaneously presses on the reservoir 100 so as to actuate the valve 200.

The device includes a trigger system that is controlled by the user inhaling, and that is for moving and/or deforming said actuator element 550 from its non-actuation position towards its actuation position, when the user inhales through the mouthpiece 400.

The trigger system includes an inhalation-sensitive member 65 that is deformable and/or movable under the effect of inhaling, the inhalation-sensitive member 65 being adapted, when it is deformed and/or moved, to move and/or deform said actuator element 550 from its non-actuation position towards its actuation position.

As described in greater detail below, the inhalation-sensitive member may be made in the form of a piston 65 that is preferably cylindrical, and that slides in a chamber 66 that is preferably cylindrical and non-deformable.

In a variant, the inhalation-sensitive member could also be made in the form of a deformable air chamber, e.g. a bellows or a deformable pouch.

FIGS. 1 to 3 show an embodiment of the invention. The actuator element is a locking element 550 that, in its non-actuation position, enables the valve member 210 of the metering valve 200 to move axially in the body 10, together with the reservoir 100, preventing said metering valve 200 from being actuated when said reservoir 100 is moved axially in the body 10 without inhaling. During inhaling, the locking element 550 is moved and/or deformed so that it prevents the valve member 210 from moving axially relative to the body 10. Thus, after inhaling, axial movement of the reservoir 100 causes the metering valve 200 to be actuated and a dose of fluid to be dispensed, synchronously with the inhaling.

The inhalation-sensitive member is made in the form of a piston 65 that slides in a chamber 66 between a rest position and an inhaling position. The chamber 66 is advantageously formed in the mouthpiece 400. Said piston 65 is connected to said locking element 550, advantageously via a rod 540. In particular, as can be seen in the figures, the locking element 550 is formed at the end of said rod 540 remote from said piston 65, and comprises an axial projection 551. A spring 67, advantageously arranged in the chamber 66, is adapted to return said piston 65 towards its rest position when there is no longer any inhaling through the mouthpiece 400.

In the non-actuation position, said projection is radially offset relative to the valve well 700, so that said valve well may move axially in the body 10, together with the valve member 210 of the metering valve 200 and the reservoir 100. Thus, in this non-actuation position, the valve member 210 does not move relative to the reservoir 100, and the metering valve 200 is thus not actuated.

When the user inhales through the mouthpiece 400, the piston 65 moves radially (relative to the movement axis of the reservoir 100 in the body 10) in the chamber 66 under the effect of the suction created by inhaling. The projection 551 is thus moved radially also, and comes to be positioned below said valve well 700, thereby forming an abutment to the downward axial movement of said valve well. As a result, the pressure exerted by the user on the bottom of the reservoir 100 moves said reservoir axially downwards in the body, and the valve well 700 that is now axially stationary relative to the body 10, thus blocks the valve member 210 of the metering valve axially relative to the body 10, so that it is driven into the valve body, thereby causing the metering valve 200 to be actuated and a dose of fluid to be dispensed.

The device shown in FIGS. 1 to 3 may also include electronic means. In particular, an electronic dose counter 1000 may be provided, advantageously assembled on the body 10. Naturally, since the reservoir 100 is movable axially in the body 10 both in the actuation position and in the non-actuation position of the actuator element 550, the dose counter 1000 cannot measure the axial movement of the reservoir 100. In this circumstance, it is preferable to use sensors that detect the dispensing of the fluid, in particular in the valve well 700, or sensors that detect the movement of the valve member 210 of the metering valve 200 relative to the valve body 201.

Preferably, the device also includes signal-transmitter means 1100 for communicating, in particular communicating remotely, information relating to the actuations of the device. In particular, the body 10 may include a signal-transmitter module, for communicating remotely with any base. Appropriate power supply means are advantageously provided.

In particular, the electronic module may advantageously comprise a card that includes an electrical switch that sends a pulse. The module may also comprise a display and/or use a Bluetooth or Wifi connection for sending information to an accompanying peripheral. Appropriate sensors, such as flowrate and/or pressure sensors, may be provided for detecting various parameters of the inhalation flow.

Associated with a dose counter 1000 that counts each dose that is actually dispensed, and with the inhalation-synchronized device of the invention, the signal-transmitter means 1100 make it possible for each dose that has been dispensed to be transmitted in completely reliable manner, e.g. to a doctor or to any other person wishing to monitor the use of the inhaler device by the user. The inhalation-synchronized device guarantees that the user inhales each time the user actuates the device, and the counter records each dose that is dispensed, together with various associated parameters, such as a timestamp for each dispensing. In this way, the doctor can know very accurately the conditions of use of the device by the user.

The present invention applies, in particular, to treating asthma attacks or chronic obstructive pulmonary disease (COPD), by using formulations of the following types: salbutamol, aclidinium, formoterol, tiotropium, budesonide, fluticasone, indacaterol, glycopyrronium, salmeterol, umeclidinium bromide, vilanterol, olodaterol, or striverdi, or any combination of these formulations.

The present invention is described above with reference to an advantageous embodiment, but naturally any useful modification could be applied thereto by the person skilled in the art, without going beyond the ambit of the present invention, as defined by the accompanying claims.

The invention claimed is:

1. An inhalation-synchronized fluid dispenser device comprising a body provided with a mouthpiece, a fluid reservoir containing a fluid and a propellant gas amounted to slide axially in said body, a metering valve including a valve member assembled on said reservoir for selectively dispensing the fluid, wherein, during actuation, said valve member is stationary relative to said body and said reservoir is moved axially relative to said body between a distal position, which is a rest position, and a proximal position, said device further comprising:
   an actuator element that is movable between a non-actuation position in which said metering valve cannot be actuated, and an actuation position in which said metering valve can be actuated; and
   an inhalation-controlled trigger system including an inhalation-sensitive member that is movable under the effect of inhaling, said inhalation-sensitive member, when moved, moving said actuator element from the non-actuation position towards the actuation position;
   wherein said actuator element is a locking element that, in the non-actuation position, enables said valve member of the metering valve to move axially in the body, together with said reservoir moving between the distal position and the proximal position, preventing said metering valve from being actuated when said reservoir is moved axially in the body without inhaling; and
   wherein, in the actuation position, said locking element prevents said valve member from moving axially relative to said body, such that, after inhaling, axial movement of said reservoir causes actuation of the metering valve.

2. A device according to claim 1, wherein, during inhaling, said locking element is moved to prevent the valve member from moving axially relative to the body.

3. A device according to claim 2, wherein said inhalation-sensitive member includes a piston that slides in a chamber between a rest position and an inhaling position.

4. A device according to claim 3, wherein said locking element is secured to a rod that is secured to the piston, so that during inhaling, said rod moves radially, moving said locking element towards the actuation position in which the locking element prevents said valve member of the metering valve from moving axially when said reservoir is moved axially in the body.

5. A device according to claim 1, including an electronic dose counter.

6. A device according to claim 1, including signal-transmitter means for communicating information relating to the actuations of the device.

7. The device according to claim 1, including signal-transmitter means for communicating remotely information relating to the actuations of the device.

8. The device according to claim 1, wherein the locking element comprises an axial projection.

9. The device according to claim 1, wherein the inhalation-sensitive member is a piston.

10. The device according to claim 1, wherein the inhalation-sensitive member is a bellows.

11. The device according to claim 6, wherein the signal-transmitter means is a signal transmitter module.

12. The device according to claim 6, wherein the signal-transmitter means comprises a display.

13. The device according to claim 6, wherein the signal-transmitter means communicates via wireless or Wifi communication.

* * * * *